United States Patent [19]

Koppe et al.

[11] Patent Number: 4,948,812

[45] Date of Patent: Aug. 14, 1990

[54] 1-PHENOXY-3-AMINO-2-PROPANOLS USE THEREOF

[75] Inventors: Herbert Koppe; Franz Esser, both of Ingelheim am Rhein, Fed. Rep. of Germany; Walter Kobinge; Christian Lillie, both of Vienna, Austria

[73] Assignee: Boehringer Ingelheim KG, Ingelheim am Rhein, Fed. Rep. of Germany

[21] Appl. No.: 125,308

[22] Filed: Nov. 25, 1987

[30] Foreign Application Priority Data

Nov. 28, 1986 [DE] Fed. Rep. of Germany ....... 3640829

[51] Int. Cl.$^5$ ................. A61K 31/165; C07C 103/133
[52] U.S. Cl. ..................................... 514/622; 514/534; 514/535; 514/597; 514/608; 514/617; 514/621; 544/165; 544/400; 546/234; 560/39; 560/142; 564/52; 564/86; 564/169; 564/17; 564/174; 564/175
[58] Field of Search .................... 564/170, 175, 52, 86, 564/169, 174; 560/39, 142; 514/617, 534, 535, 597, 608, 621, 622

[56] References Cited

PUBLICATIONS

"Chemical Abstracts", vol. 65, 1966, Col. 70996–g.
"Chemical Abstracts", vol. 72, 1970, Col. 21515y.

*Primary Examiner*—Glennon H. Hollrah
*Assistant Examiner*—James H. Turnipseed
*Attorney, Agent, or Firm*—David E. Frankhouser; Alan R. Stempel; Mary-Ellen M. Timbers

[57] ABSTRACT

Compounds of formula

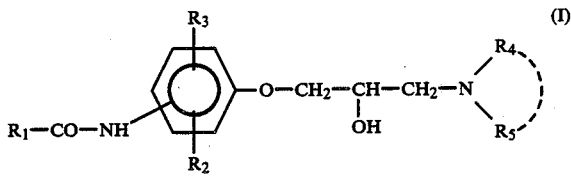

(the substituents $R_1$, $R_2$, $R_3$, $R_4$ and $R_5$ are explained in the specification) may be prepared by conventional methods.

Owing to their favorable activity profile the compounds may advantageously be used to treat certain heart and circulatory disorders.

8 Claims, No Drawings

1-PHENOXY-3-AMINO-2-PROPANOLS USE THEREOF

The invention relates to 1-aryloxy-3-amino-2-propanols, the preparation thereof in a manner known per se and their use as pharmaceutical compositions.

The new compounds are of the formula

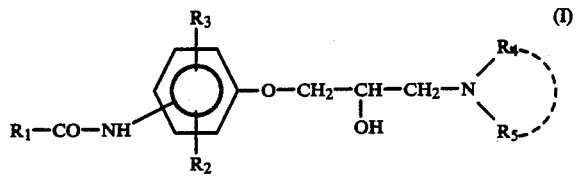

wherein $R_1$ represents a phenyl group which may optionally be substituted by one or more halogen atoms, lower alkyl, alkoxy, alkenyl, alkynyl, alkenyloxy, alkynyloxy, cycloalkyl, acyl, acyloxy, alkoxycarbonyl, hydroxyalkyl or alkoxyalkyl groups or a sulphamoyl group or the ring-binding groups —(CH=CH)$_2$—, —O—CH$_2$—O—, with bonding of the free valencies in the o-position relative to one another, or it may represent an aryloxyalkyl group which may optionally be substituted by one or more halogen atoms, lower alkyl, alkoxy, alkenyl, alkynyl, alkenyloxy, alkynyloxy, hydroxyalkyl, alkoxyalkyl, acyl, acyloxy or alkoxycarbonyl groups and the ring-forming group —(CH=CH)$_2$— or —OCH$_2$—O— with bonding of the free valencies in the o-position relative to one another, or a pyridyl group, or an anilino group which may be substituted by one or more halogen atoms or lower alkyl groups, $R_2$ represents a hydrogen or halogen atom, an alkyl or alkoxy group with 1 to 4 carbon atoms or the ring-forming groups —(CH=CH)$_2$— or —(CH$_2$)$_n$— (n=an integer from 3 to 5) with bonding of the free valencies in the o-position relative to one another, or a CN group, $R_3$ represents a hydrogen or halogen atom or an alkyl group with 1 to 4 carbon atoms, $R_4$ represents a straight-chained or branched alkyl group with 1 to 10 carbon atoms or a hydroxyalkyl group with 2 to 5 carbon atoms, and $R_5$ represents a straight-chained or branched alkyl group with 1 to 10 carbon atoms or a hydroxyalkyl group with 2 to 5 carbon atoms or a phenylalkyl group or a phenoxyalkyl group, wherein the aromatic part may be substituted by alkyl or alkoxy groups or by chlorine or bromine atoms, or $R_4$ and $R_5$ may also together with the nitrogen atom represent a heterocyclic group, e.g. a morpholine, piperidine or piperazine ring, and they may occur in the form of racemates, pure enantiomers or mixtures of enantiomers and the acid addition salts thereof.

Unless otherwise specifically stated, the general definitions are used in the following sense.

The "lower" alkyl, alkenyl, alkynyl, alkoxy, alkenyloxy and alkynyloxy groups contain up to 4 carbon atoms, as do the carbon chains in the acyl, acyloxy, alkoxycarbonyl, hydroxyalkyl or alkoxyalkyl groups. The cycloalkyl groups contain 3 to 8, preferably 5 to 7 carbon atoms. "Aryl" indicates phenyl and naphthyl, in compositions as well. "Halogen" indicates chlorine and also bromine and fluorine and, to a lesser extent, iodine.

The groups of the type specified are therefore methyl, ethyl, n-propyl, i-propyl, the butyls, allyl, propargyl and the associated -oxy groups, acyl groups such as CH$_3$CO, C$_2$H$_5$—CO and corresponding acyloxy group, alkoxycarbonyl groups such as COOC$_2$H$_5$, COOCH$_3$, COOC$_3$H$_7$, alkoxyalkyl group such as C$_2$H$_5$OC$_2$H$_4$, H$_3$C—O—CH$_2$—CH$_2$—, C$_3$H$_7$OCH$_2$, and cycloalkyl groups such as cyclopentyl and cyclohexyl.

$R_1$ preferably represents substituted phenoxymethyl groups.

$R_2$ and $R_3$ preferably represent halogen and methyl.

$R_4$ and $R_5$ preferably represent lower straight-chained or branched alkyl groups, particularly the methyl, ethyl, n-propyl or i-propyl group.

The new compounds may be prepared in a manner known per se by reacting a compound of general formula

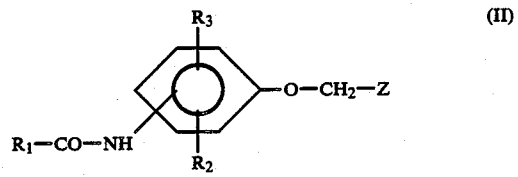

wherein $R_1$, $R_2$ and $R_3$ are defined as in formula I and Z represents the group

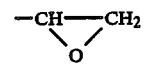

or —CHOH—CH$_2$—Hal (Hal=halogen, e.g. Cl or Br), with an amine of formula

wherein $R_4$ and $R_5$ are defined as hereinbefore.

If acid addition salts are initially obtained, these are optionally converted by conventional methods into free bases or salts of other acids. If bases are obtained initially they may, if desired, be converted into acid addition salts.

The process is preferably carried out at temperatures between 0° and 100° C., more particularly at 4° to 80° C.

The reaction media used may be alcohol or other polar solvents, e.g. methanol, ethanol, isopropanol, dioxan or tetrahydrofuran, optionally in admixture.

The starting compounds for the process according to the invention are already known or may be prepared by known methods.

The compounds according to the invention at least one asymmetric carbon atom (at the CHOH group) therefore may occur as racemates and also the form of the optical antipodes. The latter may be obtained not only by racemate separation but also with conventional auxiliary acids such as dibenzoyl (or di-p-tolyl) D-tartaric acid or D-3-bromocamphor-8-sulphonic acid or by the use of optically active starting material.

Suitable acids for the preparation of physiologically acceptable acid addition salts include, for example, hydrochloric, hydrobromic, sulphuric, methanesulphonic, maleic, acetic, oxalic, lactic or tartaric acid or 8-chlorotheophylline.

The new compounds and the physiologically acceptable acid addition salts thereof have valuable therapeutic, particularly antiarrhythmic, hypotensive or bradycardiac properties and may, on the basis of their favourable activity profile, be used advantageously, for example, to treat cardiac arrhythmia, tachycardia or high blood pressure in human medicine.

Those compounds of general formula I wherein $R_1$ represents a substituted phenoxymethyl group and $NR_4R_5$ represents a dimethylamino group, a methylethylamino group or a dimethylamino group (substituted p-phenoxyacetylaminophenoxy-3-diethyl, -methylethyl- or -dimethylamino-2-propanols) have Proved Particularly useful. Particularly valuable compounds are
1-[2,6 dimethyl 4-(2-(2,6 dimethyl-phenoxy)-acetylaminophenoxy]-2-hydroxy-3-diethylaminopropane
and 1-[2,6-dimethyl-4-(2-m-tolyloxy-acetylamino)-phenoxy]-2-hydroxy-3-diethylamino-propane.

The single dosage of the substances according to the invention is from 1 to 300 mg, preferably 10 to 150 mg (by oral route) or 1 to 20 mg (by parenteral route).

The active substances according to the invention may be made into conventional pharmaceutical preparations such as plain or coated tablets, solutions, emulsions, powders, capsules or delayed release forms, and may be produced using the normal pharmaceutical excipients and the usual methods of manufacture.

Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release such as carboxymethylcellulose, cellulose acetate phthalate or polyvinyl acetate.

The tablets may also consist of several layers. Coated tablets may be produced accordingly by coating cores made in the same way as the tablets with the substances normally used for tablet coating, such as collidone or shellac, gum arabic, talc, titanium dioxide or sugar. In order to obtain delayed release or prevent incompatibilities, the core may also consist of several layers. Similarly, the tablet coating may consist of several layers in order to obtain delayed release, and the excipients mentioned above for the tablets may be used.

Syrups of the active substances or combinations of active substances according to the invention may additionally contain a sweetener such as saccharin, cyclamate, glycerol or sugar and a flavour-enhancing agent, e.g. a flavouring such as vanillin or orange extract. They may also contain suspension adjuvants or thickeners such as sodium carboxymethylcellulose, wetting agents, e.g. condensation products of fatty alcohols with ethylene oxide, or preservatives such as p-hydroxybenzoates.

Injection solutions are prepared in the usual way, e.g. by adding preservatives such as p-hydroxybenzoates or stabilizers such as complexones and the resulting solutions are transferred into injection vials or ampoules.

Capsules containing one or more active substances or combinations of active substances may be Prepared, for example, by mixing the active substances with inert carriers such as lactose or sorbitol and encapsulating the mixture in gelatine capsules.

Suitable suppositories may be produced, for example, by mixing the active substances or combinations of active substances envisaged therefore with conventional carriers such as neutral fats or polyethylene glycol or the derivatives thereof.

EXAMPLES OF FORMULATION

| 1. Tablets | |
|---|---|
| Compound according to Example 3 | 10.0 mg |
| Corn starch | 99.0 mg |
| sec. calcium phosphate | 140.0 mg |
| Magnesium stearate | 1.0 mg |
| | 250.0 mg |

The ingredients are processed in the usual way to produce tablets weighing 250 mg.

| 2. Capsules | |
|---|---|
| Compound according to Example 1 | 150.0 mg |
| Corn starch | 150.0 mg |
| | 300.0 mg |

The finely powdered components are thoroughly mixed. 300 mg batches of the mixture are packed into conventional gelatine capsules.

The compounds according to the invention are also suitable for combining with other pharmacodynamically active substances such as diuretics, $\beta$-adrenolytics, calcium antagonists or tranquilizers.

The following Examples illustrate the invention without restricting it.

EXAMPLES OF PREPARATION

EXAMPLE 1

[1-[2,6-Dimethyl-4-(2-m-tolyloxyacetylamino)-phenoxy]-2-hydroxy-3-diethylamino-propane]hydrochloride 5 g (0.015 mol) of 1-[2,6-Dimethyl-4-(2-m-tolyloxyacetylamino)-phenoxy]-2,3-oxirane are dissolved in 80 ml of ethanol, 21 ml (0.02 mol) of diethylamine are added and the mixture is refluxed for 1.5 hours at the boiling point. After the solvent has been distilled off, the residue is dissolved in dilute hydrochloric acid and extracted with ether. The aqueous phase is made alkaline with 20% sodium hydroxide solution, extracted with methylene chloride and the organic phase is dried over sodium sulphate. The solvent is distilled off and the residue remaining is purified over a silica gel column (ethyl acetate/isopropanol/ ammonia in the ratio 70:30:2). The uniform substance isolated is dissolved in acetonitrile and the hydrochloride is crystallised out by the addition of ethereal hydrochloric acid and ether. The crystals are recrystallized from ethanol with the addition of ether.

Yield: 6.7 g, m.p. 159°–160° C.

EXAMPLE 2

[1-[2,6-Dimethyl-4-(2-m-tolyloxyacetylamino)-phenoxy]-2-hydroxy-3-piperidino-propane]hydrochloride 6 g (0.018 mol) of 1-[2,6-Dimethyl-4-(2-m-tolyloxyacetylamino)-phenoxy]propan-2,3-oxirane are dissolved in 100 ml of ethanol and after the addition of 2 ml (0.02 mol) of piperidine the mixture is refluxed for 2 hours at the boiling point. The ethanol is distilled off, the residue is dissolved in dilute hydrochloric acid, extracted with ether and made alkaline with sodium hydroxide solution. The base precipitated is taken up in methylene chloride, the organic phase is dried over sodium sulphate and the solvent is distilled off. The base is purified over a silica gel column as in Example 1. The pure substance is dissolved in acetonitrile, ethereal hydrochloric acid is added and then ether is added until crystallization begins. The colourless hydrochloride is dissolved in acetonitrile and brought to crystallization by the addition of ether.

Yield: 5.8 g, m.p.: 189°–190° C.

EXAMPLE 3

[1-[2,6-Dimethyl-4-(2-(2,6-dimethyl-phenoxy)-acetylamino)-phenoxy]-2-hydroxy-3-diethylamino-propan]hydrochloride 38.8 g of [1-[2,6-dimethyl-4-()2-(2,6-dimethyl-phenoxy)-acetylamino)-phenoxy]-2,3-oxirane are dissolved in 300 ml of ethanol and after the addition of 40 ml of diethylamine the mixture is refluxed for two hours at the boiling point. After the ethanol has been distilled off, the residue remaining is acidified with dilute hydrochloric acid and extracted with ether. The aqueous phase is made alkaline with dilute sodium hydroxide solution, the base precipitated is taken up in ether and the organic phase is dried over sodium sulphate. The ether is distilled off, the residue is purified over a silica gel column (ethylacetate/isopropanol/ammonia in the radio 70:30:5). The pure substance is dissolved in acetonitrile, ethereal hydrochloric acid and then ether are added, as a result of which the hydrochloride is precipitated in crystalline form. Crystals are dissolved in acetonitrile and ether is added until crystallization begins. 28.6 g of colourless crystals are obtained.

M.P 167°–168° C.

The compounds of formula I listed in Tables I to III are synthesized analogously to the above Examples. Unless otherwise stated, the melting points are given for the hydrochlorides.

The compounds in Table I correspond to the formula

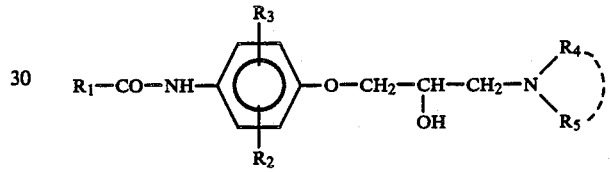

TABLE I

| Example | $R_1$ | $R_2$ | $R_3$ | $R_4$ | $R_5$ | m.p. °C. |
|---|---|---|---|---|---|---|
| 4 | CH3, with structure (tolyloxymethyl): 3-methylphenyl—O—CH2— | 2-CH3 | 6-CH3 | CH3 | CH3 | 152–153 (Base) |
| 5 | " | " | " | —CH2—CH2OH | —CH2—CH2OH | 97–99 |
| 6 | " | " | " | C3H7 | C3H7 | 126–128 |
| 7 | " | " | " | C2H5 | C3H7 | 128–131 |
| 8 | " | " | " | isoC3H7 | isoC3H7 | 128–130 |
| 9 | " | " | " | CH3 | isoC3H7 | 110–112 |
| 10 | " | " | " | C4H9 | C4H9 | 88–90 |
| 11 | " | " | " | secC4H9 | secC4H9 | 72–73 (Base) |
| 12 | " | " | " | CH3 | —C3H7 | 129–131 |
| 13 | " | " | " | CH3 | C2H5 | 138–139 |
| 14 | " | " | " | —CH2—CH=CH2 | —CH2—CH=CH2 | 122–123 |
| 15 | " | " | " | CH3 | —CH(CH3)—CH2—O—(2,6-dimethylphenyl) | 76–79 |
| 16 | " | " | " | CH3 | —CH(CH3)—CH2—O—(2,5-dichlorophenyl) | 83–86 |

TABLE I-continued

| Example | R₁ | R₂ | R₃ | R₄ | R₅ | m.p.°C. |
|---|---|---|---|---|---|---|
| 17 | " | " | " | CH₃ | -CH(CH₃)-CH₂-O-C₆H₄-OCH₃ (meta) | 70-74 |
| 18 | " | " | " | CH₃ | -CH(CH₃)-CH₂-O-C₆H₄-OCH₃ (para) | 71-75 |
| 19 | " | " | " | CH₃ | -CH(CH₃)-CH₂-O-C₆H₄-Cl (para) | 79-82 |
| 20 | 3-CH₃-C₆H₄-O-CH₂- | 2-CH₃ | 6-CH₃ | H | -CH₂-CH₂-C₆H₃(OCH₃)₂ (3,4-dimethoxy) | 127-130 (Base) |
| 21 | " | " | " | C₂H₅ | " | 90-94 |
| 22 | " | " | " | isoC₃H₇ | " | 82-85 |
| 23 | " | " | " | CH₃ | " | 80-84 |
| 24 | 2-Br-C₆H₄- | " | " | CH₃ | CH₃ | viscous oil |
| 25 | " | " | " | C₂H₅ | C₂H₅ | " |
| 26 | 2-Br-C₆H₄- | " | " | CH₃ | CH₃ | " |
| 27 | " | " | " | C₂H₅ | C₂H₅ | " |
| 28 | 2,4-Cl₂-C₆H₃-O-CH₂- | " | " | CH₃ | CH₃ | 117-118 (Base) |
| 29 | " | " | " | C₂H₅ | C₂H₅ | 101-102 (Base) |
| 30 | " | " | " | -CH₂-CH₂OH | -CH₂-CH₂OH | 104-107 |
| 31 | 2,6-(CH₃)₂-C₆H₃-O-CH₂- | 2-Cl | 6-Cl | CH₃ | CH₃ | 122-123 (Base) |
| 32 | " | " | " | CH₂H₅ | C₂H₅ | viscous oil |
| 33 | " | " | " | -C₂-CH₂OH | -CH₂-CH₂OH | 158-159 |

TABLE I-continued

| Example | R₁ | R₂ | R₃ | R₄ | R₅ | m.p. °C. |
|---|---|---|---|---|---|---|
| 34 | 2,6-dichlorophenoxymethyl | 2-CH₃ | 6-CH₃ | CH₃ | CH₃ | 171–172 |
| 35 | " | " | " | —CH₂—CH₂OH | —CH₂—CH₂OH | 102–103 (Base) |
| 36 | 3-methylphenoxymethyl | 2-Cl | 6-Cl | CH₃ | CH₃ | 91–93 (Base) |
| 37 | " | " | " | C₂H₅ | C₂H₅ | 98–99 (Base) |
| 38 | " | " | " | —CH—CH₂OH | —CH₂—CH₂OH | 139–141 (oxalate) |
| 39 | 2,4-dichlorophenoxymethyl | " | " | " | " | 149–151 |
| 40 | 2,6-dimethylphenoxymethyl | 2-CH₃ | 6-CH₃ | CH₃ | CH₃ | 190–191 |
| 41 | " | " | " | C₂H₅ | C₂H₅ | 167–168 |
| 42 | 2,6-dimethylphenoxymethyl | 2-CH₃ | 6-CH₃ | —CH₂—CH₂OH | —CH₂—CH₂OH | 164–166 |
| 43 | " | " | " | —CH₂—CH—CH₂<br>　　　　OH　OH | —CH₂—CH—CH₂OH<br>　　　　OH | 86–89 (Base) |
| 44 | " | " | " | CH₃ | —CH—CH₂—O—(2,4-dichlorophenyl)<br>CH₃ | 81–84 |
| 45 | " | " | " | CH₃ | —CH—CH₂—O—(3-methoxyphenyl)<br>CH₃ | 78–81 |

TABLE I-continued
| Example | R₁ | R₂ | R₃ | R₄ | R₅ | m.p.°C. |
|---|---|---|---|---|---|---|
| 46 | " | " | " | $CH_3$ | 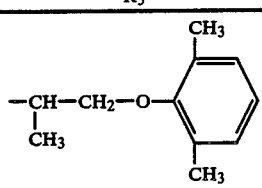 | 117–120 (oxalate) |
| 47 | " | " | " | $CH_3$ | 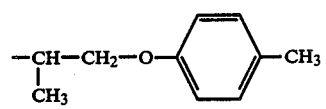 | 84–87 |
| 48 | " | " | " | $CH_3$ | 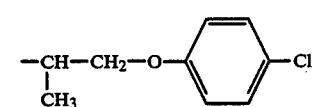 | 75–78 |
| 49 | 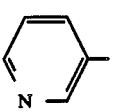 | 2-CN | H | $CH_3$ | $CH_3$ | 89–91 (Base) |
| 50 | " | " | " | $C_2H_5$ | $C_2H_5$ | 128–130 (Base) |
| 51 | 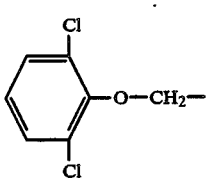 | 2-Cl | 6-Cl | $CH_3$ | $CH_3$ | 232–234 |
| 52 | " | " | " | $-CH_2-CH_2OH$ | $-CH_2-CH_2OH$ | 158–159 (Base) |
| 53 | 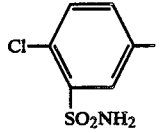 | 2-CN | " | $CH_3$ | $CH_3$ | 138–143 |
| 54 | 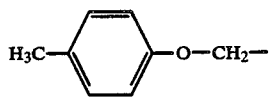 | 2-Cl | 6-Cl | $CH_3$ | $CH_3$ | 73–74 (Base) |
| 55 | " | " | " | $C_2H_5$ | $C_2H_5$ | viscous oil |
| 56 | " | " | " | $-CH_2-CH_2OH$ | $-CH_2-CH_2OH$ | 98–101 |
| 57 | 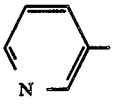 | 2-$CH_3$ | 6-$CH_3$ | $CH_3$ | $CH_3$ | 203–206 |
| 58 | " | " | " | $C_2H_5$ | $C_2H_5$ | 147–150 |
| 59 | 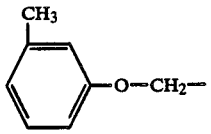 | 2-Cl | 6-Cl | $CH_3$ | $CH_3$ | 103–104 (Base) |
| 60 | " | " | " | $C_2H_5$ | $C_2H_5$ | 72–74 (Base) |

TABLE I-continued

| Example | R₁ | R₂ | R₃ | R₄ | R₅ | m.p.°C. |
|---|---|---|---|---|---|---|
| 61 | " | " | " | −CH₂−CH(OH)−CH₂OH | −CH₂−CH(OH)−CH₂OH | 97−99 (oxalate) |
| 62 | 3-methylphenyl-NH− | 2-CH₃ | 6-CH₃ | C₂H₅ | C₂H₅ | 166−167 |
| 63 | " | " | " | CH₃ | CH₃ | 158−159 |
| 64 | " | " | " | C₃H₇ | C₃H₇ | 157−158 |
| 65 | 3,4-dichlorophenyl-NH− | " | " | C₃H₇ | C₃H₇ | 183−184 (Base) |
| 66 | " | " | " | C₂H₅ | C₂H₅ | 168−169 (Base) |
| 67 | 3,4-dichlorophenyl-NH− | " | " | CH₃ | CH₃ | 180−181 (Base) |
| 68 | 4-chlorophenyl-NH− | " | " | C₂H₅ | C₂H₅ | 160−163 (Base) |
| 69 | " | " | " | CH₃ | CH₃ | 183−185 (Base) |
| 70 | " | " | " | C₃H₇ | C₃H₇ | 172−173 (Base) |
| 71 | 2,6-dimethylphenyl-NH− | " | " | C₂H₅ | C₂H₅ | 180−181 (Base) |
| 72 | " | " | " | C₃H₇ | C₃H₇ | 179−181 (Base) |
| 73 | " | " | " | CH₃ | CH₃ | 211−213 (Base) |
| 74 | 4-chlorophenyl-O−CH₂− | 2-Cl | H | C₂H₅ | C₂H₅ | 183−144 (Oxalate) |
| 75 | 2-chlorophenyl-O−CH₂− | " | " | " | " | 155−157 |
| 76 | 4-chlorophenyl-O−CH₂− | " | " | CH₃ | CH₃ | 149−150 (Oxalate) |

TABLE I-continued

| Example | R₁ | R₂ | R₃ | R₄ | R₅ | m.p.°C. |
|---|---|---|---|---|---|---|
| 77 | 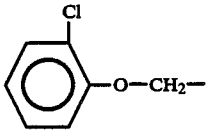 (2-Cl-phenyl-O-CH₂—) | " | " | " | " | 190–191 (Oxalate) |

Other compounds of formula

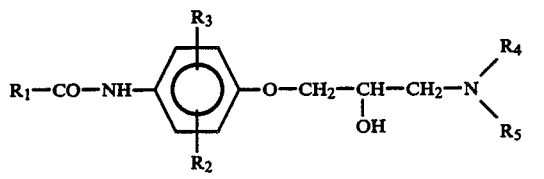

$$R_1-CO-NH-\underset{R_2}{\overset{R_3}{C_6H_3}}-O-CH_2-CH(OH)-CH_2-N\underset{R_5}{\overset{R_4}{\diagdown}}$$

according to the invention are listed in Table II.

TABLE II

| Example | R₁ | R₂ | R₃ | $-N\overset{R_4}{\underset{R_5}{\diagdown}}$ | m.p. °C. |
|---|---|---|---|---|---|
| 78 | 2-CH₃-phenyl-O-CH₂— | 2-CH₃ | 6-CH₃ | morpholino (—N(CH₂CH₂)₂O) | 190–191 |
| 79 | " | " | " | 2,6-dimethylpiperidino | 146–147 (Base) |
| 80 | " | " | " | 3,5-dimethylpiperidino | 162–164 |
| 81 | 2-Cl-5-SO₂NH₂-phenyl | 2-CN | H | 4-methylpiperazin-1-yl | 244–246 |

Table III

The compounds included in this Table according to the invention correspond to the formula

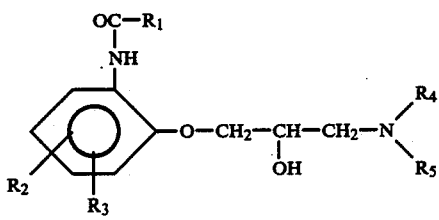
| Example | R1 | R2 | R3 | R4 | R5 | m.p. °C. |
|---|---|---|---|---|---|---|
| 82 | 2,6-dimethylphenoxymethyl (CH3, CH3 on phenyl with O-CH2-) | H | H | CH3 | CH3 | 150-2 |
| 83 | " | H | H | i-C3H7 | H | 144-6 |
| 84 | " | H | H | C2H5 | C2H5 | 111-2 |
| 85 | " | H | H | n-C3H7 | H | 114-5 |
| 86 | 2,5-dimethylphenoxymethyl | H | H | i-C3H7 | H | 184-5 |
| 87 | " | H | H | CH3 | CH3 | 171-3 |
| 88 | " | H | H | n-C3H7 | H | 157-8 |
| 89 | 2-chlorophenoxymethyl | H | H | C2H5 | C2H5 | 136-8 |
| 90 | 2,5-dimethylphenoxymethyl | H | H | t-C4H9 | H | 159-60 |
| 91 | 2,6-dimethylphenoxymethyl | 6-CH3 | H | C2H5 | C2H5 | 150-1 |
| 92 | 2,6-dichlorophenoxymethyl | H | H | CH3 | CH3 | 124-5 (Oxalate) |
| 93 | 2,6-dimethylphenoxymethyl | 6-CH3 | H | i-C3H7 | CH3 | 156-7 |

-continued

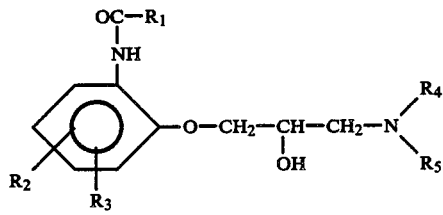

| Example | R₁ | R₂ | R₃ | R₄ | R₅ | m.p. °C. |
|---|---|---|---|---|---|---|
| 94 | " | 6-CH₃ | H | CH₃ | CH₃ | 146-8 (Oxalate) |
| 95 | " | 6-CH₃ | H | t-C₄H₉ | H | 169-70 |
| 96 | " | H | H | t-C₄H₉ | H | 180-1 |
| 97 | 2,5-dimethylphenoxymethyl | H | H | C₂H₅ | C₂H₅ | 139-40 |
| 98 | 2,6-dichlorophenoxymethyl | H | H | n-C₃H₇ | H | 145-147 (Oxlate) |
| 99 | " | H | H | t-C₄H₉ | H | 157-9 |
| 100 | " | H | H | i-C₃H₇ | H | 132-3 |
| 101 | 2,6-dimethylphenoxymethyl | 6-CH₃ | H | n-C₃H₇ | H | 101-2 |
| 102 | 2,5-dimethylphenoxymethyl | 6-CH₃ | H | C₂H₅ | C₂H₅ | 113-50 |
| 103 | " | 6-CH₃ | H | i-C₃H₇ | H | 153-6 |
| 104 | " | 6-CH₃ | H | CH₃ | CH₃ | 122-3 |
| 105 | " | 6-CH₃ | H | t-C₄H₉ | H | 189-91 |
| 106 | " | 6-CH₃ | H | n-C₃H₇ | H | 128-30 |
| 107 | 2,6-dichlorophenoxymethyl | 6-CH₃ | H | C₂H₅ | C₂H₅ | 146-8 |
| 108 | " | 6-CH₃ | H | t-C₄H₉ | H | 130-2 |
| 109 | " | 6-CH₃ | H | i-C₃H₇ | H | 152-4 (Oxalate) |
| 110 | " | 6-CH₃ | H | CH₃ | CH₃ | 132-3 (Oxalate) |
| 111 | " | 6-CH₃ | 6-CH₃ | C₂H₅ | C₂H₅ | |
| 112 | " | 3-CH₃ | H | C₂H₅ | C₂H₅ | |

-continued

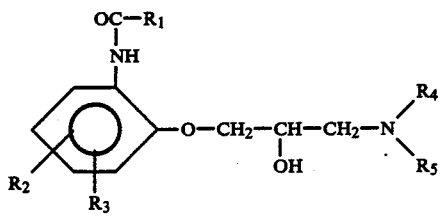

| Example | R₁ | R₂ | R₃ | R₄ | R₅ | m.p. °C. |
|---------|----|----|----|----|----|----------|
| 113 | 2,3-dimethylphenoxymethyl (CH₃, CH₃ on ring with O—CH₂—) | 4-CH₃ | 6-CH₃ | C₂H₅ | C₂H₅ | |
| 114 | " | 5-CH₃ | H | C₂H₅ | C₂H₅ | |
| 115 | 3-methylphenoxymethyl (CH₃ on ring with O—CH₂—) | 4-CH₃ | 6-CH₃ | CH₃ | n-C₃H₇ | |

Pharmacological trials

The compounds according to the invention were investigated according to C. Lillie et al., Drug Research 35, 301-305 (1985).

Isolated guinea pig hearts according to Langendorff, moist weight 1.0–1.2 g, perfused with standard tyrode (31° C., saturated with $O_2 + 2\%$ $CO_2$) under constant pressure (60 cm $H_2O$). After destruction of the sinus node region at the right atrium, electrical ventricular stimulation with rectangular pulses (1 mA, 10 msec) at 2.5 Hz. Bias 2 g, contractions recorded isometrically.

Perfusion with tyrode containing the test substance (concentration given in mcg ml) was carried out for 30 min.

The table given the changes as a percentage of the previous values ($\Delta\%$) of the ECG parameters of ST and QRS and the contraction amplitude and the throughflow at the end of the period of perfusion with the tyrode containing the test substance. po The results for some of the compounds tested are shown in the following Table.

| Compound | mcg/ml | ST | QRS | changes ($\Delta\%$) after 0 min. contractility | throughflow |
|----------|--------|----|----|-----|------|
| Example 1 | 1 | +39 | +4 | −31 | +5 |
| Example 12 | 1 | +38 | +5 | −23 | −2 |
| Example 41 | 1 | +31 | +2 | −9 | +5 |

As the values in the Table show, the ST level is significantly increased, as desired, but the QRS level and the throughflow are only slightly increased.

What is claimed is:

1. A compound of formula

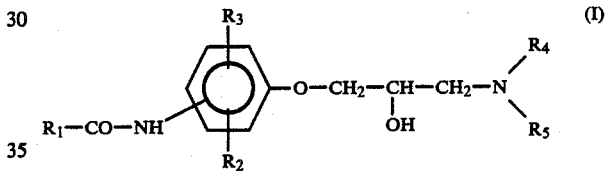

wherein
$R_1$ represents a phenyl group which may optionally be substituted by one or more halogen atoms, lower alkyl, alkoxy, alkenyl, alkynyl, alkenyloxy, alkynyloxy, cycloalkyl, acyl, acyloxy, alkoxycarbonyl, hydroxyalkyl or alkoxyalkyl groups or a sulphamoyl group, or it may represent an aryloxyalkyl group which may optionally be substituted by one or more halogen atoms, lower alkyl, alkoxy, alkenyl, alkynyl, alkenyloxy, alkynyloxy, hydroxyalkyl, alkoxyalkyl, acyl, acyloxy or alkoxycarbonyl groups,
$R_2$ represents a halogen atom, an alkyl or alkoxy group with 1 to 4 carbon atoms or a CN group,
$R_3$ represents a halogen atom or an alkyl group with 1 to 4 carbon atoms,
$R_4$ represents a straight-chained or branched alkyl group with 1 to 10 carbon atoms or a hydroxylakyl group with 2 to 5 carbon atoms, and
$R_5$ represents a straight-chained or branched alkyl group with 1 to 10 carbon atoms or a hydroxylakyl group with 2 to 5 carbon atoms or a phenylalkyl group or a phenoxyalkyl group, whilst the aromatic pat may be substituted by alkyl or alkoxy groups or by chlorine or bromine atoms, or
a pharmaceutically acceptable acid addition salt thereof.

2. A compound as claimed in claim 1, wherein $R_1$ is a substituted phenoxymethyl group, $R_2$ and $R_3$ represent halogen, cyano or methyl, and one of them may also represent hydrogen, and $R_4$ and $R_5$ represent lower straight-chained or branched alkyl groups.

3. A compounds as claimed in claim 1 or 2, wherein $R_1$—CO—NH is in the 4-position of the phenoxy group, $R_1$ represents a phenoxymethyl group, mono- or disubstituted by methyl, $R_2$ and $R_3$ represent chlorine or methyl, and $R_4$ and $R_5$ represent methyl, ethyl, n-propyl or i-propyl, wherein $R_2/R_3$ and $R_4/R_5$ may be identical or different.

4. [1-[2,6-Dimethyl-4-(2-m-tolyloxyacetylamino)-phenoxy]-2-hydroxy-3-diethylamino-propane]hydrochloride or a pharmaceutically acceptable acid addition salt thereof.

5. [1-[2,6-Dimethyl-4-(2-(2,6-dimethyl-phenoxy)-acetylamino)-phenoxy]-2-hydroxy-3-diethylamino-propan]hydrochloride or a pharmaceutically acceptable acid addition salt thereof.

6. 1-[2,6-Dimethyl-4-[2-(3-methylphenoxy)-acetylamino]phenoxy]-2-hydroxy-3-methyl-n-propylaminopropane or a pharmaceutically acceptable acid addition salt thereof.

7. A pharmaceutical composition comprising a compound as claimed in claim 1 together with conventional excipients and/or carriers.

8. A method for treating cardiac arrhythmia, tachycardia or high blood pressure which comprises administering an antiarrhythmic, bradycardiac or hypotensive amount of a compound according to claims 1,2,3,4,5 or 6.

* * * * *